United States Patent
Bjorling et al.

(10) Patent No.: US 7,546,161 B1
(45) Date of Patent: Jun. 9, 2009

(54) METHODS FOR LOSS OF CAPTURE AND FUSION AVOIDANCE IN BIVENTRICULAR PACING THERAPY

(75) Inventors: Anders Bjorling, Solna (SE); Xiaoyi Min, Thousand Oaks, CA (US); Richard Williamson, Saugus, CA (US); Karin Jarverud, Solna (SE); Nils Holmstrom, Jarfalla (SE)

(73) Assignee: Pacesetter, Inc., Sylmar, CA (US)

( * ) Notice: Subject to any disclaimer, the term of this patent is extended or adjusted under 35 U.S.C. 154(b) by 554 days.

(21) Appl. No.: 11/330,316

(22) Filed: Jan. 11, 2006

(51) Int. Cl.
  *A61N 1/368* (2006.01)
(52) U.S. Cl. ............................... 607/28; 607/9; 607/25
(58) Field of Classification Search ................ 607/9, 607/11, 27, 28, 25
  See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 5,476,483 A | 12/1995 | Bornzin et al. | 607/17 |
| 6,314,323 B1 | 11/2001 | Ekwall | 607/23 |
| 6,324,427 B1* | 11/2001 | Florio | 607/28 |
| 6,456,881 B1* | 9/2002 | Bornzin et al. | 607/27 |
| 6,456,882 B1 | 9/2002 | Schloss | |
| 6,505,071 B1 | 1/2003 | Zhu et al. | |
| 6,553,259 B2 | 4/2003 | Mouchawar et al. | |
| 6,871,096 B2 | 3/2005 | Hill | 607/25 |
| 6,970,743 B2* | 11/2005 | Weinberg et al. | 607/25 |
| 7,353,061 B2* | 4/2008 | Hedberg et al. | 607/9 |
| 2001/0049543 A1* | 12/2001 | Kroll | 607/28 |
| 2003/0083700 A1 | 5/2003 | Hill | 607/9 |
| 2003/0195579 A1 | 10/2003 | Bradley et al. | 607/27 |
| 2004/0082975 A1* | 4/2004 | Meyer et al. | 607/27 |
| 2004/0158293 A1* | 8/2004 | Yonce et al. | 607/9 |
| 2004/0260351 A1 | 12/2004 | Holmstrom et al. | 607/27 |
| 2005/0075676 A1 | 4/2005 | Deno et al. | |
| 2005/0209649 A1* | 9/2005 | Ferek-petric | 607/17 |

FOREIGN PATENT DOCUMENTS

EP  1 430 930 A1  6/2004

OTHER PUBLICATIONS

NonFinal Office Action, mailed Sep. 3, 2008: Related U.S. Appl. No. 11/330,315.

* cited by examiner

*Primary Examiner*—Carl H Layno
*Assistant Examiner*—Luther G Behringer

(57) ABSTRACT

An exemplary method includes delivering biventricular pacing therapy using one or more timing parameters, detecting loss of capture, deciding if fusion exists without adjusting the one or more timing parameters and, based on the deciding, calling for fusion avoidance or calling for a capture threshold search. Various other exemplary methods, devices, systems, etc., are also disclosed.

11 Claims, 9 Drawing Sheets

METHODS FOR LOSS OF CAPTURE AND FUSION AVOIDANCE IN BIVENTRICULAR PACING THERAPY

FIELD OF THE INVENTION

Subject matter disclosed herein generally relates to cardiac pacing or stimulation therapy. Various exemplary technologies pertain to detecting loss of capture and fusion in biventricular pacing therapy and other pacing related therapy.

BACKGROUND

In the normal heart, the ventricles pump at the about the same time in a manner synchronized with the atria. When a patient has heart failure, often times the right and left ventricles do not pump together, which is referred to as dysynchrony. If dysynchrony is significant, the heart has less time to fill with blood and cardiac output drops.

Biventricular pacing therapy and, in particular, cardiac resynchronization therapy (CRT), aims to synchronize the right and left ventricles via delivery of appropriately timed stimulation to each ventricle. With respect to such timed stimulation, various parameters are involved, including atrio-ventricular delay and interventricular delay. Clinical studies related to biventricular cardiac pacing therapy have shown that use of an optimal atrio-ventricular delay (e.g., AV delay) and an optimal interventricular delay (e.g., VV delay) can improve cardiac performance. However, such optimal delays depend on a variety of factors.

Optimization of AV delay or VV delay may occur at implantation and sometimes, a re-optimization may occur during a follow-up consultation. Recently, techniques have been disclosed for optimization algorithms that may periodically re-optimize without any intervention. Regardless of where, who or what performs an optimization or re-optimization, the health of the CRT patient should be a concern as timings should not be adjusted without a substantial purpose for doing so.

Conventional implantable devices typically include algorithms that respond to a condition by adjusting one or more timings. For example, as fusion beats are sometimes detected as loss of capture, a single detection of loss of capture does not necessarily mean that the stimulation amplitude is too small and that a capture threshold search needs to be conducted; instead, a fusion beat could also have occurred. Thus, conventional implantable devices typically implement an automatic fusion avoidance response after the first loss of capture to rule out the possibility of initiating a threshold search on a fusion beat. In general, such conventional fusion avoidance algorithms increase the AV or PV delays in dual-chamber devices and reset the basic interval on the backup pulse in single chamber devices. As already mentioned, for heart failure patients undergoing CRT, AV and VV delays are of very high importance and should be adjusted only if needed or circumstances permit doing so without substantial detriment to the patient. Thus, a need exists for fusion detection or other techniques to distinguish true loss of capture from fusion without a need to change timings. Various exemplary technologies presented herein address this need and other needs.

SUMMARY

An exemplary method includes delivering biventricular pacing therapy using one or more timing parameters, detecting loss of capture, deciding if fusion exists without adjusting the one or more timing parameters and, based on the deciding, calling for fusion avoidance or calling for a capture threshold search. Various other exemplary methods, devices, systems, etc., are also disclosed.

In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Exemplary Stimulation Device

The techniques described below are intended to be implemented in connection with any stimulation device that is configured or configurable to stimulate nerves and/or stimulate and/or shock a patient's heart.

Figure 1:
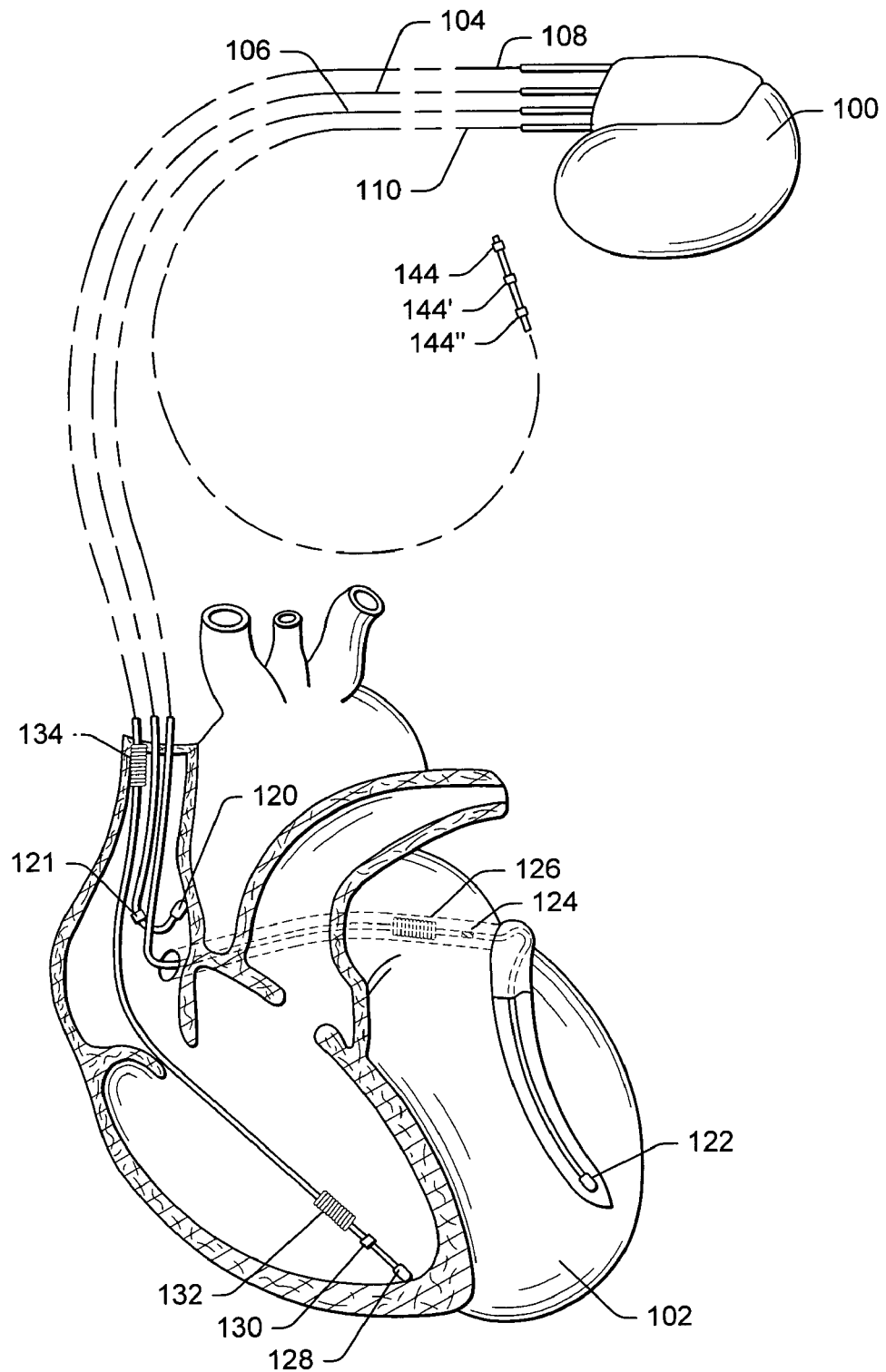
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. Suitable devices for implementation of various exemplary technologies described herein may have the same or a different number of leads or types of leads, etc. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
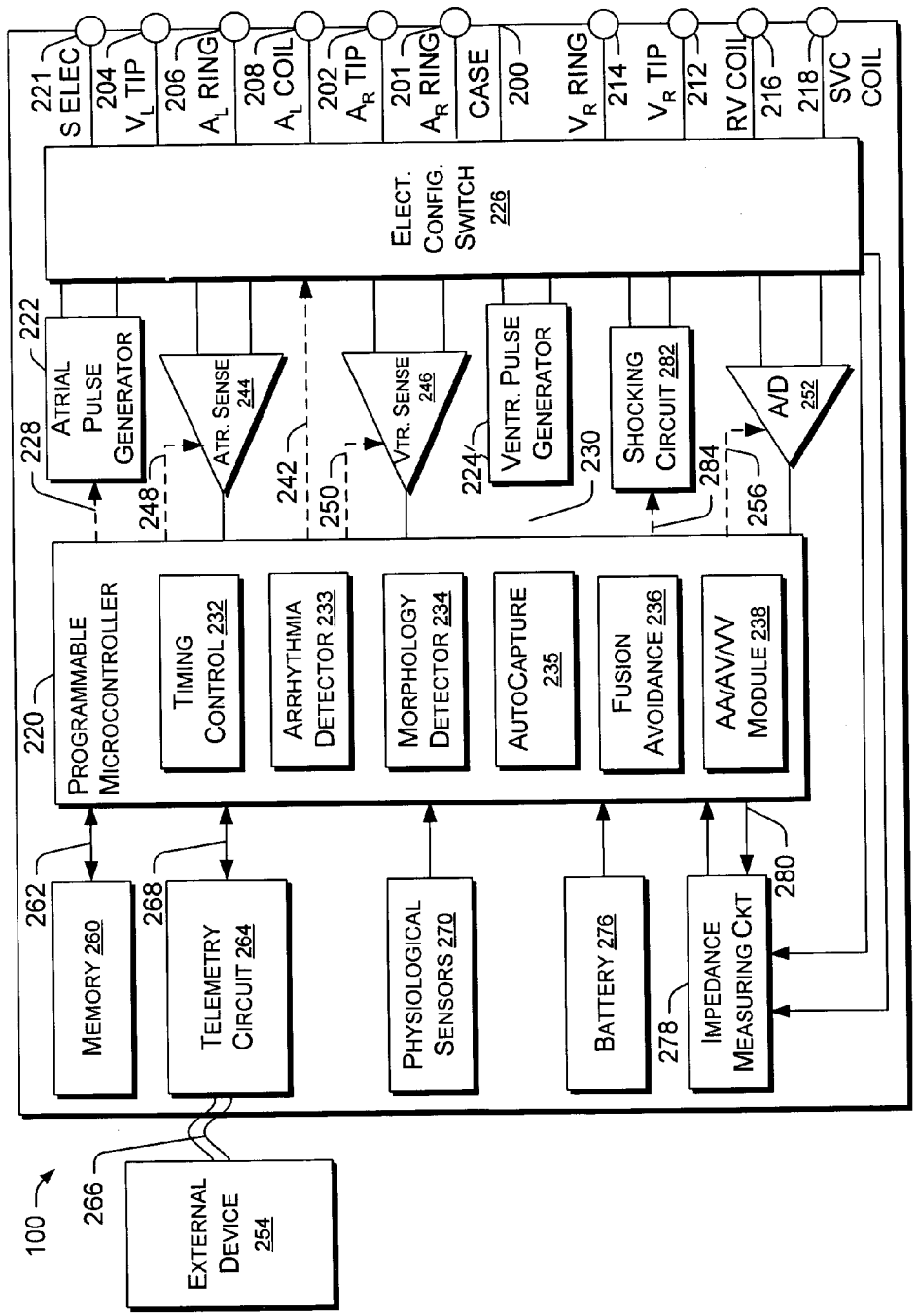
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administers stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used, that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 233, a morphology detector 234, an automatic capture module 235 (e.g., AUTOCAPTURE™ algorithm), a fusion avoidance module 236 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an M delay, AV delay and/or VV delay module 238 for performing a variety of tasks related to AA delay, AV delay and/or W delay. This component can be utilized by the stimulation device 100 for determining desirable times to administer various therapies, including, but not limited to, ventricular stimulation therapy, biventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. For example, such a module may include capabilities related to analysis of IEGMs (e.g., slopes, amplitudes, etc.) and/or determining cardiac performance, especially as it may relate to one or more pacing parameters.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electro-mechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

The stimulation device additionally includes a battery 276 (e.g., a power source) that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an, impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythms

Figure 3:
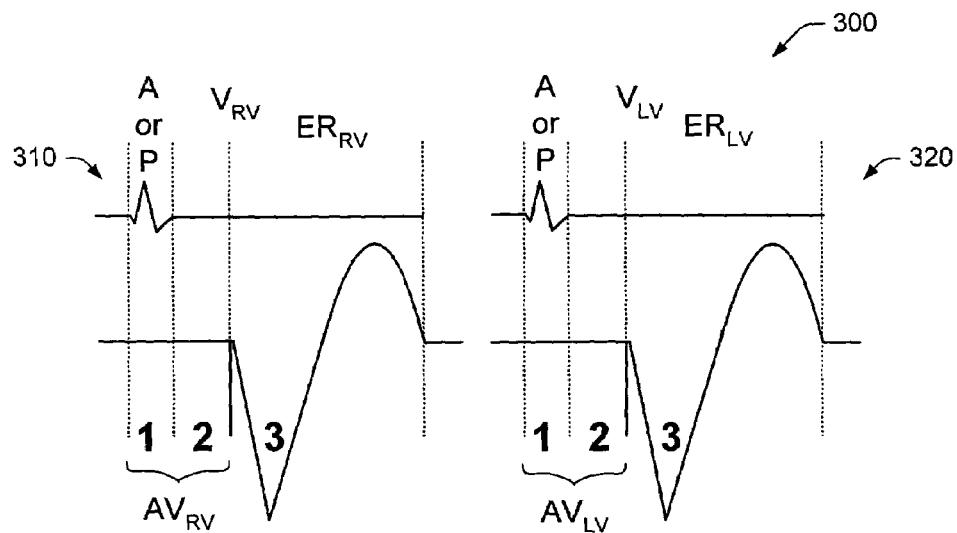
FIG. 3 is an exemplary plot of aortic velocity time integral versus a programmed interventricular conduction delay and exemplary equations for a parameter $\alpha$.
Figure 3:
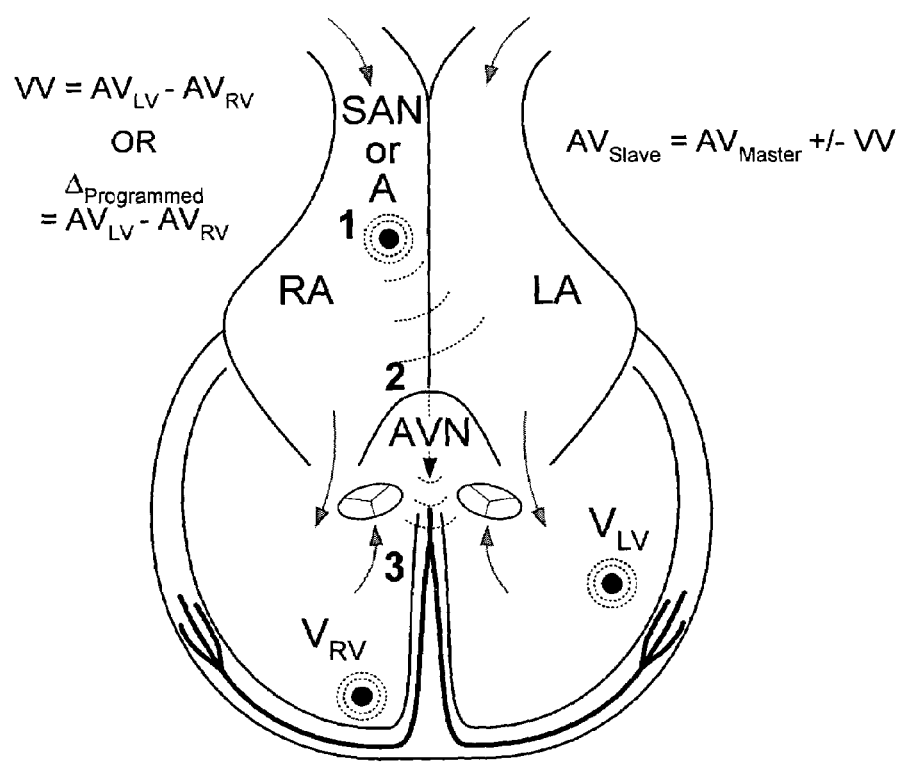

FIG. 3 shows an approximate anatomical diagram of a heart and two sets of waveforms 300. One set of waveforms 310 corresponds in part to right ventricular activity while another set of waveforms 320 corresponds in part to left ventricular activity. Action potentials propagating through a normal heart typically occur as follows: 1, associated with the sinoatrial node (SAN) and the atria; 2, associated with the atrio-ventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches. However, ventricular pacing may override an atrial paced or intrinsic stimulus or may allow for ventricular stimulation and contraction where AVN conduction is impaired. Thus, in this example, ventricular rhythm typically relies on ventricular stimulation.

Referring again to the heart diagram, for ventricular pacing, action potentials may propagate through the heart as follows: 1, associated with a paced atrial stimulus or an intrinsic SAN stimulus and the atria; 2, associated with the atrio-ventricular node (AVN); and 3, associated with a paced right ventricle ($V_{RV}$) and a paced left ventricle ($V_{LV}$). In an atrial paced heart (A), cells depolarize near a pacing site (1) and thereby initiate an action potential (shown as dashed lines emanating from the pacing site). This action potential propagates rapidly through the atria (which contract) and depending on cardiac condition, may propagate through the AVN (2) and then to the ventricles (3). Various cardiac conditions are discussed further below where propagation of an atrial action potential is impaired or otherwise unable to cause adequate ventricular contraction.

Implantable devices capable of biventricular pacing typically have a single atrial sensing channel and typically one or two ventricular channels (e.g., optionally one switchable channel that can switch between sensing in the left ventricle and the right ventricles and/or one ventricle and both ventricles). Often detection of an R wave or an evoked response relies on signal amplitude or signal derivative with respect to time. Further, many detection methods are capable of assigning a time to a detected R wave or evoked response or assigning a time span to an A wave to R wave or evoked response interval.

The waveforms 310, 320 represent information obtained via surface electrocardiograms (ECG). An implantable device such as the device 100 may acquire similar information in the form of intracardiac electrocardiograms (IEGMs). In the plots 310, 320, intrinsic atrial depolarization is represented as a "P wave" and atrial depolarization responsive to atrial stimulation (A) is represented as an "A wave". Similarly, intrinsic ventricular depolarization is represented as an "R wave", or QRS complex while ventricular depolarization responsive to ventricular stimulation (V) is represented as an evoked response (ER) (e.g., capture).

The waveform 310 shows a P wave or an A wave followed by right ventricular stimulation ($V_{RV}$) and a responsive right ventricular evoked response ($ER_{RV}$). The timing between delivery of atrial stimulation and delivery of right ventricular stimulation is referred to as the AV interval, and in this example, a right ventricular AV interval ($AV_{RV}$). The timing between intrinsic atrial depolarization and delivery of right ventricular stimulation is referred to as the right ventricular PV interval ($PV_{RV}$). In some instances, the right AV interval may be based on a sensed atrial depolarization rather than the timing of atrial stimulation.

The waveform 320 shows a P wave or an A wave followed by left ventricular stimulation ($V_{LV}$) and a responsive left ventricular evoked response ($ER_{LV}$). The timing between delivery of atrial stimulation and delivery of left ventricular stimulation is referred to as the AV interval, and in this example, a left ventricular AV interval ($AV_{LV}$). The timing between intrinsic atrial depolarization and delivery of left ventricular stimulation is referred to as the left ventricular PV interval ($PV_{LV}$). In some instances, the left AV interval may be based on a sensed atrial depolarization rather than the timing of atrial stimulation.

In general, biventricular pacing (e.g., cardiac resynchronization therapy) aims to synchronize contraction of the right and left ventricles. For example, if optimal cardiac function occurs when the right and left ventricles contract simultaneously, then $AV_{RV}$ and $AV_{LV}$ are equal, for example, when based on the same atrial stimulation.

A biventricular pacing parameter, known as the interventricular interval (VV), corresponds to the timing between contraction of the right ventricle and left ventricle. In general, VV is defined as $AV_{LV}$-$AV_{RV}$ and, where the ventricles contract simultaneously, VV is zero. While some patients may have optimal cardiac function when the ventricles do not contract simultaneously, $VV_{optimal}$ is typically less than about +/−10 ms.

A variable referred to as Δ represents an intrinsic interventricular delay that is based on an atrio-ventricular delay for the left ventricle (e.g., $AR_{LV}$, $PR_{LV}$) and an atrio-ventricular delay for the right ventricle (e.g., $AR_{RV}$, $PR_{RV}$). For example, $AR_{LV}$-$AR_{RV}$. The actual value or the absolute value of the variable Δ may be used in determining cardiac condition.

The variable Δ is often used in assessing whether a patient may benefit from biventricular pacing therapy. For example, a long interventricular delay may be indicative of a conduction block; left bundle branch block (LBBB) may cause the left ventricle to contract more than approximately 50 ms after contraction of the right ventricle (e.g., Δ>0); whereas, a right bundle branch block (RBBB) may be expected to cause the right ventricle to contract well after the left ventricle (e.g., Δ<0). Of course, a patient may have RBBB and LBBB of similar extent such that interventricular delay does not indicate whether a block could be RBBB or LBBB. In such circumstances, atrio-ventricular delay may indicate block.

Significant asynchronous ventricular contraction (e.g., non-optimal VV delay) may in some instances impair cardiac function. Thus, as described herein, various exemplary techniques aim to maintain adequate synchrony or otherwise maintain a substantially optimal VV delay. Various exemplary techniques may maintain or adjust W or AV (e.g., $AV_{RV}$, $AV_{LV}$, $PV_{RV}$, $PV_{RV}$, AV, PV) to provide adequate cardiac function. Such exemplary techniques are useful in instances where a change occurs in cardiac condition, performance of an implantable device, or one or more interfaces between an implantable device and the body.

The variable Δ is measurable and the optimal value is denoted $Δ_{optimal}$. The programmable parameter VV may be programmed to substantially match $Δ_{optimal}$; sometimes the programmed parameter VV is referred to herein as $Δ_{programmed}$ (e.g., $AV_{LV}$-$AV_{RV}$ or $PV_{LV}$-$PV_{RV}$). Thus, a $Δ_{programmed}$ value less than zero indicates that for bi-ventricular pacing, a pacing stimulus or stimuli was delivered to the left ventricle prior to the right ventricle. A $Δ_{programmed}$ of zero indicates that both $AV_{RV}$ and $AV_{LV}$ or $PV_{RV}$ and $PV_{LV}$ were set to approximately equal AV or PV times, which may optionally be an overall optimal time (e.g., $AV_{optimal}$ and $PV_{optimal}$).

In some instances, a parameter AV or PV is set and assigned to one ventricle, for example, a "master" ventricle. In such instances, VV (or $Δ_{programmed}$) is used to determine the timing of the other ventricle, which may be referred to as a "slave" ventricle. Thus, at least two parameters are typically specified (e.g., $AV_{Master}$ and W, $AV_{RV}$ and AVLV, etc.) Various techniques exist to set biventricular pacing parameter.

Handling Loss of Capture for Biventricular Pacing Therapy

Various exemplary methods described herein pertain to loss of capture for biventricular pacing therapy (e.g., CRT). In particular, a threshold search typically occurs in response to a "loss of capture" determination (LOC).

Capture may be defined as a cardiac depolarization induced by a stimulus or output pulse; the resulting capture may also be termed an "evoked response". Another term, "capture threshold" is typically defined as the lowest output setting that results in stable and consistent capture. While capture may be reported in terms of energy, charge and current density, these cannot be directly or easily measured nor directly programmed in a clinical setting. Often, capture threshold is defined by programmable options of a pacing device or system. Many pacing systems report capture threshold in terms of pulse amplitude (e.g., volts) or pulse duration (e.g., milliseconds). Another term for pulse duration is pulse width. Where voltage is mentioned with respect to output stimulation settings for particular algorithms, energy may be inferred and hence other suitable manners to increase energy output may be substituted.

Figure 4:
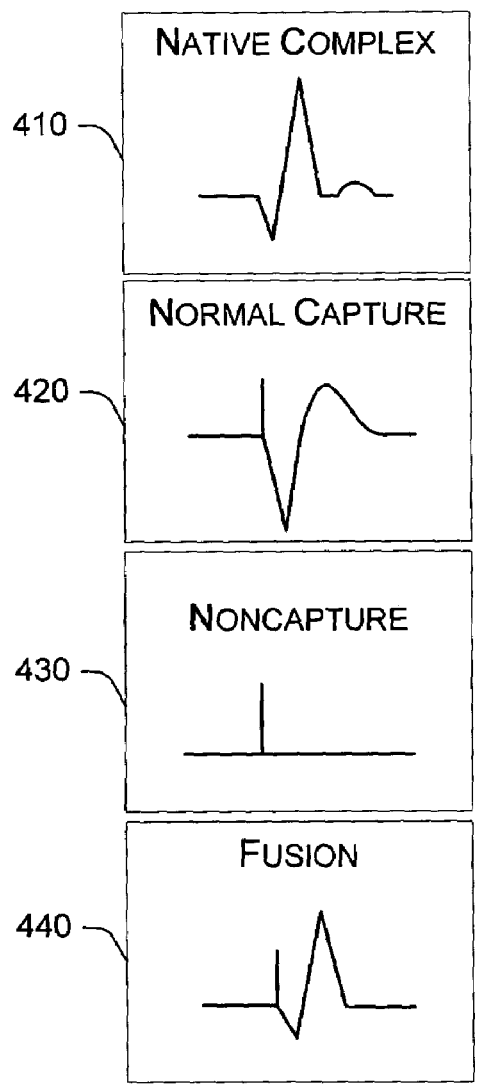
FIG. 4 is a plot of a potential signal versus time (IEGM) for an evoked response.

FIG. 4 shows various exemplary waveforms 400 that include a native waveform 410 (e.g., per an ECG), which exhibits a distinct QRS complex and a distinct T wave; a paced ventricular waveform 420 that results in capture (i.e., an evoked response); a stylized non-capture waveform 430 with a stimulation artifact, for example, resulting from the ventricles being refractory at the time of stimulation or use of an insufficient stimulation energy (intracardiac electrograms (IEGMs) acquired with use of a blanking interval may not exhibit such an artifact); and a fusion waveform 440, which is typically characterized by a wave complex formed by depolarization of the myocardium initiated by both a non-native stimulus and a native or conducted stimulus. As described herein, a waveform indicative of fusion may be referred to as a "fusion beat".

Fusion can confound loss of capture determinations. As already mentioned, fusion is typically characterized by a wave complex formed by depolarization of the myocardium initiated by two different foci, commonly a non-native stimulus as from a pacemaker or ICD and a native or conducted stimulus. Fusion is primarily a timing-related issue; consequently, where fusion is the underlying cause for a loss of capture determination, a need does not exist for adjustment of stimulation energy via a threshold search.

Conventional threshold search algorithms typically include one or more fusion avoidance features. For example, if loss of capture is diagnosed following a primary stimulation pulse, then a back-up pulse is delivered and, on the next cycle, the AV delay (or PV delay) is extended (e.g., by approximately 100 ms). An inference is then made that the diagnosed loss of capture is due to fusion if a R wave is detected within this extended AV delay (or PV delay). Throughout this description AV may include PV where "A" represents an atrial event (intrinsic or electrically stimulated).

When such an approach is implemented in conjunction with biventricular pacing, the adjustment to the AV delay (or PV delay) can have a detrimental effect on the therapy. For example, optimal AV (or PV) and VV settings are often interdependent. Hence, a change in AV may cause VV to be non-optimal. At worse, the VV may be inadequate and cause a significant decrease in cardiac output, thereby resulting in patient discomfort or deterioration in patient quality of life. Again, patients undergoing CRT are typically in higher New York Heart Association (NYHA) classes and have weaker hearts. As such, they may respond negatively to any substantial shift away from an optimal biventricular pacing setting.

When compared to single ventricular pacing therapies, biventricular therapies offer an opportunity for more instances of fusion and loss of capture. Loss of capture or fusion may occur in the right ventricle, the left ventricle or both. Further, fusion in the left ventricle may be due to stimulation in the right ventricle or due to stimulation in the left ventricle and fusion in the right ventricle may be due to stimulation in the left ventricle or due to stimulation in the right ventricle. For example, referring again to FIG. 3, consider a biventricular therapy where stimulation of the left ventricle (VLV) occurs prior to stimulation of the right ventricle (VRV). In this example, an activation front emanating from the left ventricle may fuse with right ventricular stimulation. Such fusion may result in a loss of capture indication.

As described herein, various exemplary techniques account for fusion in a manner can avoid a need for adjustment to biventricular pacing settings. In particular, various exemplary techniques implement a fusion detection algorithm prior to calling for any change in stimulation energy, for Example, as associated with a capture threshold search. Such exemplary techniques optionally account for the different types of fusion that can occur in biventricular pacing therapy.

An exemplary method commences following detection of loss of capture to determine if fusion exists. If fusion exists, then it is highly likely that fusion was the underlying cause of the loss of capture determination. Again, fusion is primarily a timing related issue; therefore, where fusion exists, there is typically no need to adjust stimulation energy. If fusion does not exist, then the loss of capture detection is most likely due to inadequate stimulation energy. A capture threshold search may then proceed without a need to adjust the biventricular pacing settings.

Figure 5:
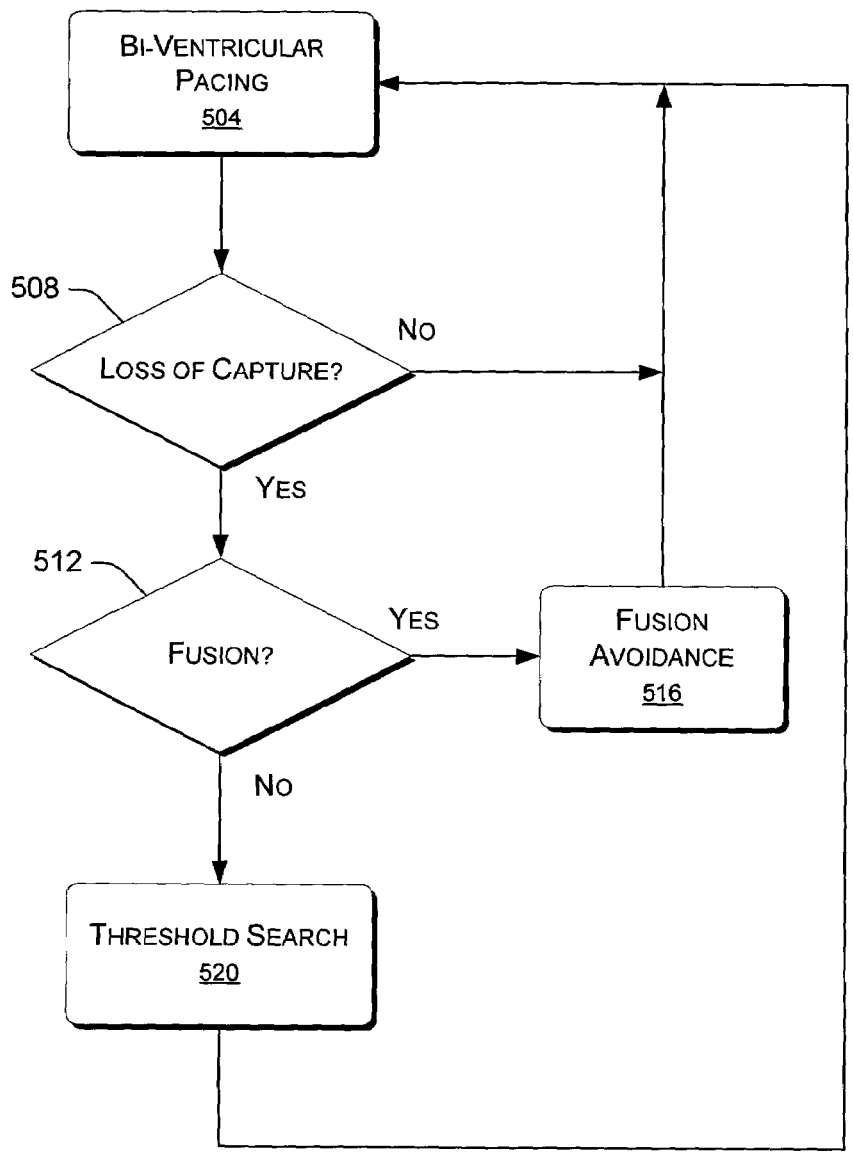
FIG. 5 is a plot of normalized maximum slope for an evoked response versus normalized stroke volume where stroke volume increases with decreasing maximum slope.

FIG. 5 shows an exemplary method 500 that aims to avoid unnecessary adjustments to one or more biventricular pacing settings. The method 500 commences in a biventricular pacing block 504 where various settings are used to delivery stimulation to at least the right ventricle and the left ventricle. Such settings may include, for example, AV, VV, $AV_{RV}$, $AV_{LV}$, etc.

The method 500 continues in a decision block 508 that decides if loss of capture has occurred. Loss of capture may be decided or detected in any of a variety of manners. In general, loss of capture based at least in part on amplitude of sensed cardiac activity, a slope of sensed cardiac activity, etc. For example, a capture detection algorithm may rely on deciding whether a sufficient negative slope and a sufficient negative amplitude exist. In this example, if either condition is not present, then the algorithm decides that a loss of capture occurred. However, referring to the stylized waveforms 420 and 440 of FIG. 4, the fusion waveform 440 may not meet such criteria and, in turn, the algorithm may indicate a loss of capture.

If the decision block 508 indicates that no loss of capture occurred, then the method 500 continues with the biventricular pacing (e.g., returns to normal operation block 504). However, if the decision block 508 detects loss of capture, then the method 500 enters another decision block 512 that decides if fusion exists. This decision may occur by any of a variety of techniques, some of which are described further below.

If the decision block 512 decides that fusion exists, then there is no need to adjust the stimulation energy. Instead, the method 500 enters a fusion avoidance block 516 that, for example, adjusts one or more timings to avoid fusion. However, if the decision block 512 decides that fusion does not exist, then the method 500 continues in a threshold search block 520. The threshold search block 520 seeks to regain capture by increasing stimulation energy, optionally without changing any biventricular timing parameter values.

Most threshold search algorithms determine a capture threshold and then set stimulation energy in excess of the capture threshold by some "safety" margin. While the use of a such a margin expends more energy than needed for capture, it may reduce the need for threshold searches. A capture threshold search for any stimulation site may occur according to a schedule or in response to any of a variety of conditions. As discussed herein, the most common condition calling for a threshold search in conventional biventricular pacing devices is typically loss of capture. Various exemplary techniques address such situations.

Figure 6:
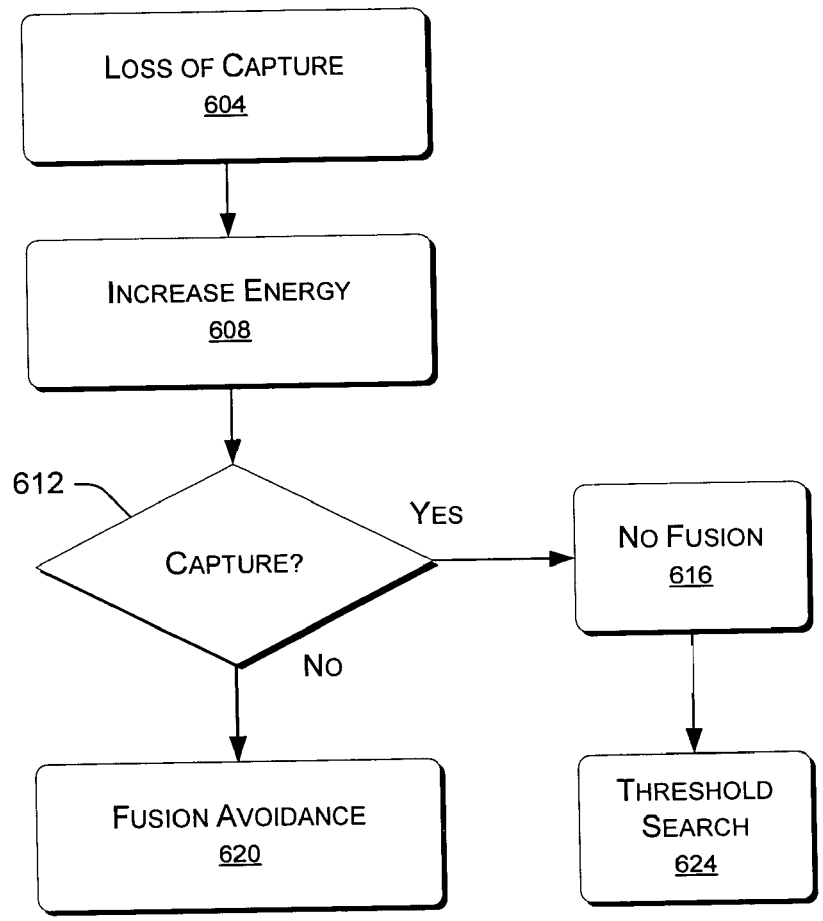
FIG. 6 is a diagram of an exemplary method that includes conditions precedent to determining one or more pacing parameters based on evoked response information.

FIG. 6 shows an exemplary method 600 that responds to loss of capture in biventricular pacing therapy. The method 600 commences with a loss of capture detection block 604 that detects loss of capture at one or more stimulation sites. The method 600 responds to loss of capture in an increase energy block 608 that increases stimulation energy at the particular site or sites where loss of capture was detected. A decision block 612 follows that decides if capture exists for stimulation delivered using the increased stimulation energy per block 608. If the capture exists per the decision block 612, then the method 600 continues in the "no fusion" block 616 and then a threshold search block 624 that performs a threshold search to determine a threshold or otherwise determine a proper stimulation energy for the site in question. If the decision block 612 decides capture did not occur given the higher stimulation energy, then the method 600 enters a fusion avoidance block 620. The fusion avoidance block 620 calls for one or more techniques that aim to avoid fusion. Such techniques typically require an adjustment to timing.

Where the loss of capture block 612 notes that loss of capture has been detected at more than one site, then the exemplary method 600 may loop through various blocks, as appropriate. For example, the method may loop through the increase energy block 608 and decision block 612 for each site to determine if fusion exists at any of the sites and they take appropriate action. In such an example, if fusion exists at one of the sites, then a change in timing may be required. Under such circumstances, it may be expeditious to forego checking for fusion at the other sites. In another example where loss of capture has been detected at more than one site, the block 608 increases the stimulation energy at all sites and then decides per the decision block 612 if capture occurred at all of the sites.

An exemplary implantable device (see, e.g., the device 100 of FIGS. 1 and 2) may include a power source, a circuit for acquisition of intracardiac electrograms, a processor powered by the power source, memory accessible by the processor and control logic, operable through use of the processor, to implement the exemplary method 600. For example, control logic may call for delivery of energy from the power source according to one or more biventricular pacing therapy timing parameters (e.g., AV, VV, etc.), to detect capture after delivery of the energy based on at least one acquired intracardiac electrogram, to decide if fusion exists without a need to adjust the one or more timing parameters and, in response thereto, to call for fusion avoidance or to call for a capture threshold search.

Figure 7:
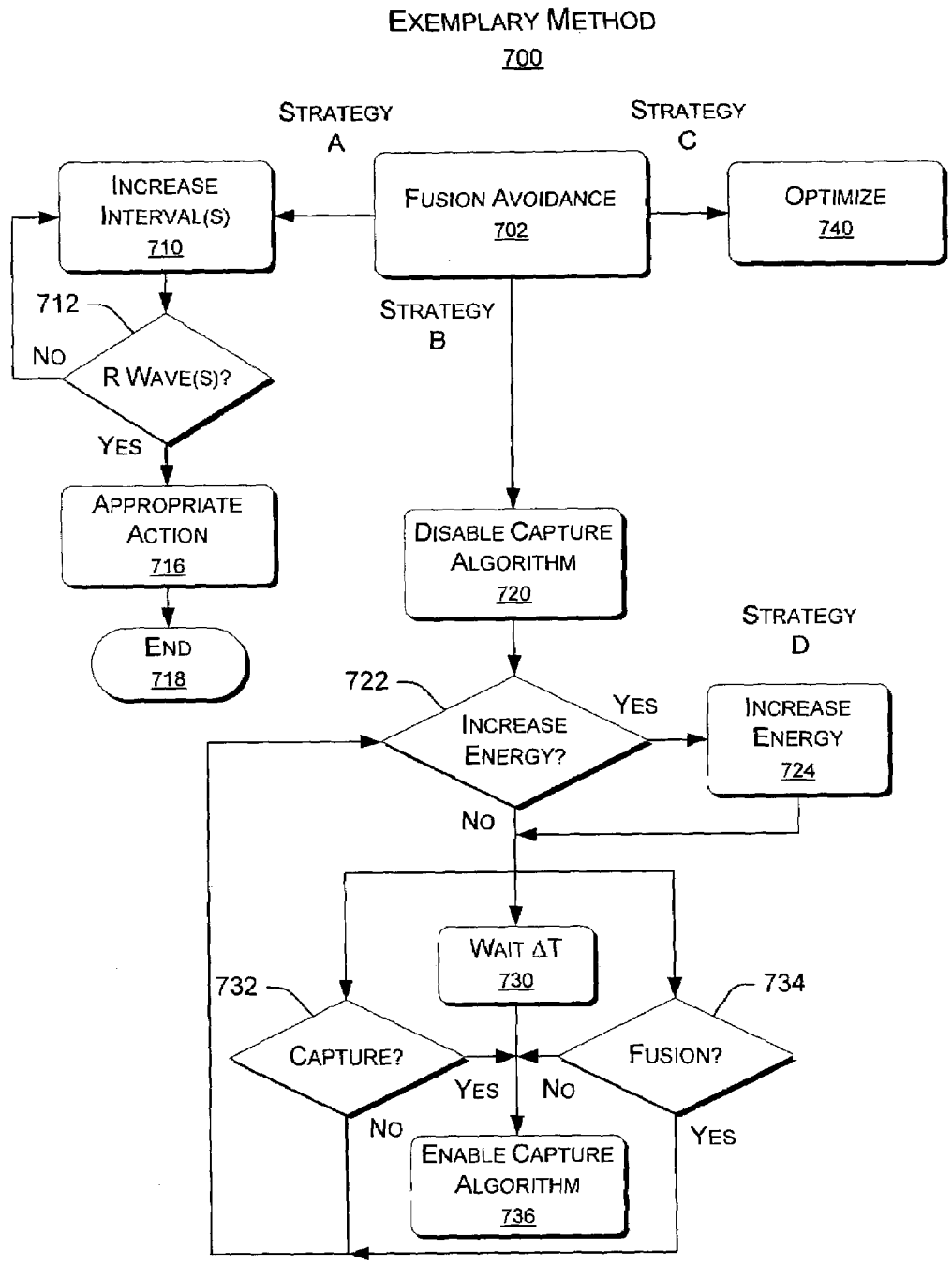
FIG. 7 is a diagram of an exemplary method that includes more than one adjustment loop for adjusting pacing parameters based on IEGM information such a maximum slope of an evoked response.

FIG. 7 shows an exemplary method 700 that includes various strategies for fusion avoidance: Strategies A, B, C and D. Such strategies may be called by a fusion avoidance block 702 (see, e.g., the fusion avoidance block 620 of FIG. 6).

Strategy A commences in an interval adjustment block 710 that increases one or more intervals. For example, if fusion is indicated in the right ventricle, then one or more intervals (e.g., AV, VV, $AV_{RV}$, etc.) are increased such that the delivery of stimulation to the right ventricle is delayed. The increased interval allows more time for intrinsic conduction from the atria or of other origin. Strategy A continues in a decision block 712 that decides if an R wave was detected prior to delivery of stimulation. If an R wave or R waves are detected, then Strategy A uses such information to take appropriate action per the action block 716. For example, appropriate action may occur if negative hysteresis is enabled where a sensed event will cause the delay in question to be decreased and thereby avoid the fusion; if instead, positive hysteresis is enabled, the delay remains prolonged as intrinsic conduction is favored. Strategy A terminates in an end block 718.

Strategy B commences in a block 720 that disables an autocapture algorithm. Such an autocapture algorithm may be a conventional capture algorithm that aims to ensure that capture occurs and that calls for fusion avoidance via one or more timing changes. A decision block 722 follows whereby a decision as to whether to increase stimulation energy. If the decision block 722 decides to increase stimulation energy, then an increase energy block 724, which is also labeled Strategy D, a subset of Strategy B.

According to Strategy B, a capture algorithm is disabled 720, an increase in stimulation energy does not occur and the biventricular timings remain undisturbed. Again, since fusion exists (per the fusion avoidance block 702), disabling the capture algorithm prevents unnecessary threshold searches. According to Strategy B, the capture algorithm is re-enabled in an enablement block 736 after one of three actions determined by a capture decision block 732, a wait block 730 and a fusion decision block 734.

The capture decision block 732 decides if capture exists and, if so, then Strategy B enters the enablement block 736. In this instance, fusion no longer exists. However, if the decision block 732 decides that capture does not exist, then Strategy B may return to the decision block 722 and decide to pursue Strategy D, i.e., per the increase energy block 722 to increase stimulation energy, if possible, or other action may be taken.

The wait block 730 causes a wait of Δt, which is essentially a duration for which the capture algorithm is disabled. After expiration of this timer, Strategy B enters the enablement block 736 to enable the capture algorithm.

The fusion decision block 734 decides if fusion still exists, for example, via a fusion detector. If fusion does not exist, then Strategy B enters the enablement block 736 to enable the capture algorithm. However, if fusion does exist per the decision block 734, then Strategy B continues at the decision block 722 where Strategy D or other action may be taken.

According to Strategy D, a capture algorithm is disabled 720, an increase in stimulation energy occurs (per block 724) and the biventricular timings remain undisturbed. By increasing stimulation energy, the risk of any true loss of capture is reduced. Again, since fusion exists (per the fusion avoidance block 702), disabling the capture algorithm prevents unnecessary threshold searches. According to Strategy D, the capture algorithm is re-enabled in an enablement block 736 after one of three actions determined by a capture decision block 732, a wait block 730 and a fusion decision block 734.

The capture decision block 732 decides if capture exists at the increased energy and, if so, then Strategy D enters the enablement block 736. In this instance, fusion no longer exists. However, if the decision block 732 decides that capture does not exist, then Strategy D may return to the increase energy block 722 to further increase stimulation energy, if possible, or other action may be taken.

The wait block 730 causes a wait of Δt, which is essentially a duration for which the capture algorithm is disabled. After expiration of this timer, Strategy D enters the enablement block 736 to enable the capture algorithm.

The fusion decision block 734 decides if fusion still exists, for example, via a fusion detector. If fusion does not exist, then Strategy D enters the enablement block 736 to enable the capture algorithm. However, if fusion does exist per the decision block 734, then Strategy D continues at the decision block 722 where a further increase in energy per a loop of Strategy B may occur or other action may be taken.

Strategy C includes an optimization block 740 where optimization occurs for one or more timing parameters related to biventricular pacing therapy (e.g., AV, VV etc.). Such an optimization may optionally switch to pacing of a single ventricle. In either instance, Strategy C aims to avoid fusion by adjusting one or more pacing related parameters. Any of a variety of optimization techniques may be used for Strategy C.

As already mentioned, fusion is typically undesirable, however, fusion can provide useful information. In some instances, biventricular pacing therapy parameters may be deemed "optimal" yet fusion occurs in one of the ventricles. For example, if the interventricular conduction delay is about 50 ms and the VV parameter set to about 30 ms, then fusion may occur in the later stimulated or slave ventricle due to stimulation of the earlier stimulated or master ventricle ("VV" fusion). In such situations, a conventional beat to beat autocapture algorithm may be unable to effectively operate in the ventricle experiencing fusion. Hence, in broader terms, this situation may be deemed not optimal. Further, should such a situation arise, an exemplary method may use the fusion information as an indicator that one or more of the biventricular pacing therapy parameters are not optimal and call for a parameter optimization. In other situations, fusion may occur in the slave ventricle due to an atrial event thus fusion may be classified as $AV_{Master}$ fusion and/or $AV_{Slave}$ fusion (or $AV_{Master}$ fusion, $Vu_{lvae}$ fusion and/or a combination of these types).

An exemplary method optionally adjusts or limits the VV parameter based on an interventricular conduction delay to thereby avoid the aforementioned VV fusion scenario. For example, where the VV parameter is sufficiently less than the interventricular conduction delay, then the aforementioned VV fusion scenario may be avoided (e.g., where VV is constrained as being no more than about 70% to 80% of the interventricular conduction delay).

As already mentioned, fusion from an atrial event may occur. AV and VV may be adjusted to avoid such fusion. For example, if fusion occurs in the slave ventricle due in part to an atrial event, then the VV delay and/or the AV delay may be reduced in an effort to avoid fusion whereas if fusion occurs in the master ventricle due in part to an atrial event, then the AV delay for the master may be reduced in an effort to avoid fusion. An exemplary device optionally implements an algorithm that can step through reductions in AV delay and/or VV delay to avoid fusion due in part to an atrial event. In general, a patient may tolerate larger changes in AV delay than in VV delay. For example, based on optimal target AV delay and VV delay, an AV delay range of +/−25 ms and a VV delay range of +/−10 ms may be tolerable for a particular patient. Thus, an exemplary method may adjust AV delay prior to any adjustment to VV delay in an effort to avoid fusion.

In some instances, a pacing electrode or electrodes for the right ventricle may be positioned close to a pacing electrode or electrodes for the left ventricle. Given such a scenario, fusion may occur at short VV delay (e.g., VV less than about 5 ms). An exemplary method may use a short VV delay to determine if RV and LV electrodes are close or to estimate a distance between various electrodes.

Knowledge of blocks such as bundle branch block (e.g., left or right) may be used by an exemplary method to respond more effectively to fusion scenarios. For example, a patient with left bundle branch block (LBBB) is unlikely to experience fusion in the LV due directly in part to an atrial event and hence fusion in the LV is likely to be VV fusion. The same reasoning applies to right bundle branch block (RBBB). Thus, given knowledge of blocks, an exemplary method may be streamlined for avoiding a limited set of fusion scenarios. For example, a set of adjustments for AV delay and/or VV delay may exist for a RBBB patient and another set of adjustments for AV delay and/or VV delay may exist for a LBBB patient. For patients with certain degrees of AV block, other exemplary methods may rely on corresponding sets of adjustments (e.g., for a high degree of AV block, recognition of VV fusion and associated avoidance techniques).

An exemplary method may avoid fusion due to an atrial event by adjusting AV or PV (AV fusion, $AV_{slave}$ fusion and $AV_{Master}$ fusion or PV fusion, $PV_{slave}$ fusion, $PV_{Master}$ fusion). In general, a parameter such as AV can be selected from a greater range of delay times than a parameter such as VV. For example, a suitable AV can typically be between about 100 ms and about 300 ms whereas a suitable VV can typically be between about 5 ms to about 30 ms (master to slave). Consequently, as already mentioned, it may be easier to adjust an AV parameter to avoid AV fusion than to adjust a VV parameter to avoid VV fusion. As described herein, various exemplary methods can address VV fusion and optimize one or more biventricular pacing parameter given, for example, one or more VV fusion constraints.

Figure 8:
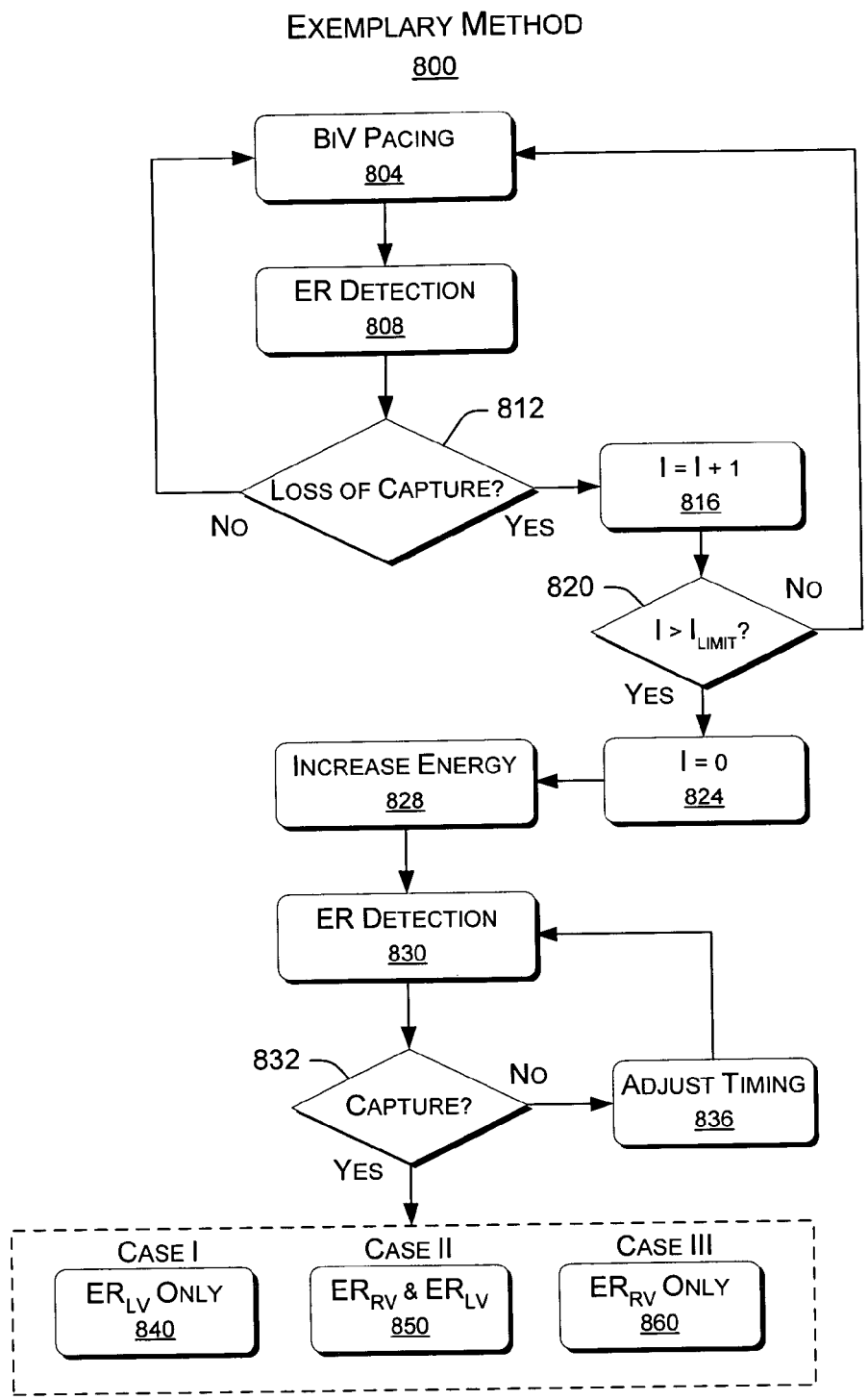
FIG. 8 is a diagram of an exemplary method for deciding when to adjust one or more pacing parameter based on evoked response information.

FIG. 8 shows an exemplary method 800 for addressing loss of capture issues in biventricular pacing therapy. The method 800 commences in a biventricular pacing therapy block 804. An evoked response detection block 808 follows. Such a block operates to acquire and analyze information related to cardiac activity. A decision block 812 then decides if the information or analysis of the evoked response detection block 808 is indicative of capture or loss of capture. If the decision block 812 decides that loss of capture did not occur, then the method 800 continues at the biventricular pacing therapy block 804. However, if the decision block 812 decides that loss of capture occurred, then the method 800 continues in a block 816 that increments an index "I".

The index "I" is used to determine how many times loss of capture is noted, for example, during a particular time period or given a certain number of cardiac cycles. In the example of FIG. 8, a decision block 820 compares the index to a limit ($I_{Limit}$) to decide if the limit has been exceeded. If the decision block 820 decides that the limit has not been exceed, then the method 800 returns to the biventricular pacing therapy block 804. However, if the limit has been exceeded (e.g., given certain criteria, etc.), then the method 800 continues in a reset block 824 that resets the counter and appropriate action follows.

According to the exemplary method 800, when loss of capture occurs ($I_{Limit}$+1) times, an operational block 828 increases stimulation energy. An evoked response detection block 830 acquires information and then a decision block 832 decides if capture occurred. If the decision block 832 decides that capture has not occurred, then an adjustment block 836 adjusts one or more timings related to pacing therapy and the method 800 continues at the ER detection block 830. Once capture does occur, however, the decision block 832 continues in one of three action blocks 840, 850, and 860 described as Case I, Case II and Case III. Case I 840 pertains to a capture for the left ventricle only ($ER_{LV}$ only), Case II 850 pertains to capture for both ventricles ($ER_{RV}$ and $ER_{LV}$) and Case III 860 pertains to capture for the right ventricle only ($ER_{RV}$ Only)

Figure 9:
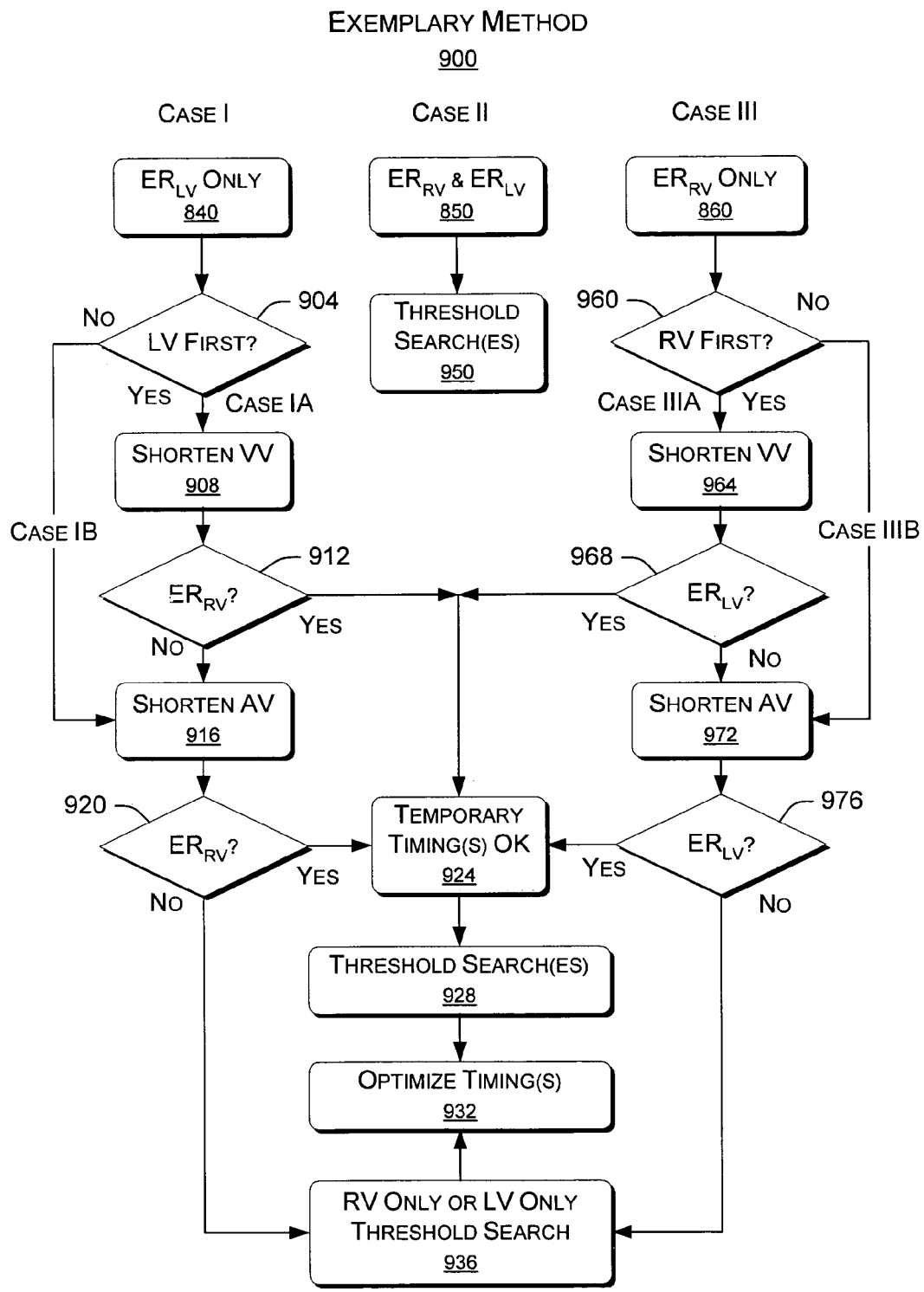
FIG. 9 is a diagram of a tiered optimization scheme that optionally includes more than one method of optimizing one or more pacing parameters.

FIG. 9 shows an exemplary method 900 that includes three branches that correspond to Cases I, II and III. These branches commence in the aforementioned block 840, 850 and 860, which are also shown in FIG. 9. Case I includes variants Case IA and Case IB, depending on whether the biventricular pacing therapy calls for pacing the left ventricle first (Case IA) or the right ventricle first (Case IB). A decision block 904 makes this decision and directs the method to the appropriate action. If the RV is first, Case IB, then the method continues in an adjustment block 916 that shortens the AV delay, which will cause stimulation for the RV to be delivered early in an effort to avoid fusion. However, if the LV is first, Case IA, then the method continues in an adjustment block 908 that adjusts VV, for example, shortening VV by setting VV to zero or another short time delay (e.g., less than about 5 ms). This acts to eliminate the possibility that stimulation delivered to the LV is causing fusion in the right ventricle. Adjustment to the VV setting could also occur through use of an interventricular conduction delay. For example, by pacing one ventricle and sensing in the other, a delay time may be determined, referred to herein as an interventricular conduction delay. An exemplary algorithm may adjust the VV to be, for example, less than about 80% of the interventricular conduction delay to the ventricle in question, noting that the right-to-left and left-to-right interventricular conduction delays may differ.

Both Case IA and IB seek to avoid fusion and detect capture in the right ventricle. As such, Case IA continues in a decision block 912 that decides if an evoked response (i.e., capture) exists in the right ventricle ($ER_{RV}$). If so, then the method continues to a temporary timings acceptance block 924 to maintain the timings and proceed to a threshold search block 928 that causes one or more threshold searches to occur without adjustment to the temporary timings. Again, an adjustment to stimulation energy is appropriate via the block 928 because of the operational block 828 of FIG. 8 caused an increase in stimulation energy. Optimization of one or more timings then occurs in an optimization block 932.

However, if the decision block 912 indicates that the adjustment to VV did not result in detection of capture in the right ventricle, then the method continues in the adjustment block 916, as occurred for Case IB. Again, the adjustment block 916 shortens the AV timing in an effort to avoid fusion in the right ventricle.

A decision block 920 follows the adjustment block 916 to decide if an evoked response occurred in the right ventricle ($ER_{RV}$). If the decision block 920 decides that such a response occurred, then the method continues in the aforementioned temporary timings acceptance or maintenance block 924 and so forth, as described above.

However, in the instance the decision block 920 decides that an evoked response (i.e., capture) did not occur in the right ventricle, then the method enters a threshold search block 936 that performs threshold searches for the right ventricle only or for the left ventricle only (i.e., single ventricle pacing is used for the search(es)). After the search block 936, the method continues in the optimization block 932 to optimize the timings for biventricular pacing or other pacing, as appropriate.

Case II corresponds to capture in both ventricles. However, as stimulation energy was increased per block 828 of FIG. 8, a threshold search(es) block 950 occurs to adjust stimulation energy, as appropriate. While various blocks refer to threshold search(es), adjust of stimulation energy may occur without actually uncovering a threshold. For example, if a minimum energy limit is set, and the implantable device captures at the minimum energy limit, all that is known is that the actual capture threshold is less than the minimum energy limit.

Case III includes variants Case IIIA and Case IIIB, depending on whether the biventricular pacing therapy calls for pacing the right ventricle first (Case IIIA) or the left ventricle first (Case IIIB). A decision block 960 makes this decision and directs the method to the appropriate action. If the LV is first, Case IIIB, then the method continues in an adjustment block 972 that shortens the AV delay, which will cause stimulation for the LV to be delivered early in an effort to avoid fusion. However, if the RV is first, Case IIIA, then the method continues in an adjustment block 964 that adjusts VV, for example, shortening VV by setting VV to zero or another short time delay (e.g., less than about 5 ms). This acts to eliminate the possibility that stimulation delivered to the RV is causing fusion in the left ventricle.

Both Case IIIA and IIIB seek to avoid fusion and detect capture in the left ventricle. As such, Case IIIA continues in a decision block 968 that decides if an evoked response (i.e., capture) exists in the left ventricle ($ER_{LV}$). If so, then the method continues to the temporary timings acceptance block 924 to maintain the timings and proceed to a threshold search block 928 that causes one or more threshold searches to occur without adjustment to the temporary timings. Again, an adjustment to stimulation energy is appropriate via the block 928 because of the operational block 828 of FIG. 8 caused an increase in stimulation energy. Optimization of one or more timings then occurs in an optimization block 932.

However, if the decision block 968 indicates that the adjustment to VV did not result in detection of capture in the right ventricle, then the method continues in the adjustment block 972, as occurred for Case IIIB. Again, the adjustment block 972 shortens the AV timing in an effort to avoid fusion in the left ventricle.

A decision block 976 follows the adjustment block 972 to decide if an evoked response occurred in the left ventricle ($ER_{LV}$). If the decision block 976 decides that such a response occurred, then the method continues in the aforementioned temporary timings acceptance or maintenance block 924 and so forth, as described above.

However, in the instance the decision block 976 decides that an evoked response (i.e., capture) did not occur in the left ventricle, then the method enters a threshold search block 936 that performs threshold searches for the right ventricle only or for the left ventricle only (i.e., single ventricle pacing is used for the search(es)). After the search block 936, the method continues in the optimization block 932 to optimize the timings for biventricular pacing or other pacing, as appropriate.

An exemplary method may include delivering biventricular pacing therapy using an AV delay and a VV delay wherein pacing occurs first in a master ventricle and second in a slave ventricle, detecting loss of capture in one of the ventricles and shortening the AV delay if the loss of capture occurred in the master ventricle to reduce risk of fusion or shortening the VV delay if the loss of capture occurred in the slave ventricle to reduce risk of fusion. In such an exemplary method, the shortening the AV delay reduces risk of fusion between a ventricular stimulus and an atrial event and the shortening the VV delay reduces risk of fusion between a ventricular stimulus and a ventricular event (see, e.g., Case IA, Case IIIA and Case IB, Case IIIB of the method 900 of FIG. 9).

An exemplary device may include a power source, a circuit for acquisition of intracardiac electrograms, a processor powered by the power source, memory accessible by the processor and control logic, operable through use of the processor, to implement the aforementioned exemplary method and optionally other exemplary methods described herein.

In general, for CHF patients receiving a biventricular pacing device for CRT, AV and VV delays are of very high importance. Thus, a need exists for fusion detection or other techniques to distinguish true loss of capture from fusion without changing the delays. Various exemplary algorithms call for a capture threshold search only if a fusion detector indicates that the beat was not a fusion beat.

An exemplary fusion detector may run in parallel with an evoked response detector, where, for example, every beat is analyzed by the fusion detector. Alternatively, such an exemplary fusion detector is triggered by the evoked response detector whereby the fusion detector is only used on stimulation pulses resulting in detection of loss of capture. An exemplary fusion detector optionally uses an IEGM morphology, T wave presence, threshold history, PDI values or other technique(s) for detection of fusion.

An exemplary fusion detector operates as follows: when the loss of capture is detected, the amplitude of the succeeding pacing pulse is set very high (e.g. 4.5 V). The biventricular pacing delays are left unchanged. If the high amplitude pulse captures, this is an indication that the threshold has been changed and that fusion is not present. However, if the high amplitude pulse does not achieve capture, this is an indication that fusion is present. Various exemplary fusion detectors act in a manner whereby changes to a biventricular pacing timing parameter need not occur.

Various exemplary methods pertain to capture recovery. Such exemplary method optionally start at a high energy level (e.g., 4.5 V) and search down, in an effort to minimize duration of loss of capture for a patient undergoing biventricular pacing therapy. Such exemplary methods optionally forego a capture recovery phase. A general goal is to minimize use of non-optimal biventricular pacing timings particularly where such non-optimal timings compromise cardiac performance (e.g., hemodynamic performance).

Various exemplary methods described herein respond to fusion. Such exemplary methods include exemplary method 900 of FIG. 9. While various exemplary methods pertain to biventricular pacing therapy, adaptation may occur for atrial loss of capture and fusion.

Various exemplary methods are optionally implemented for patients that experience a high frequency of threshold searches. Further, various exemplary methods may be implemented under certain conditions, such as time of day. Most CRT patients need proper timings during the day, hence, such exemplary methods may be implemented during the day only, for example, in response to an activity level per an activity sensor. At night or at rest, CRT patients typically have a higher tolerance for non-optimal timing settings. Hence, an exemplary method may include an activity or time of day trigger that enables or disables specialized mechanisms that aim to avoid adjustment to CRT timings (e.g. AV, VV, PV, etc.).

An exemplary method includes delivering biventricular pacing therapy using an AV delay and a VV delay, determining patient activity level (e.g., using a sensor and/or time) and, based on the patient activity level enabling or disabling automatic adjustment of the AV delay or the VV delay. Such a method may enable such automatic adjustments (e.g., automatic via an adjustment algorithm that can occur without direct care provider interaction) when a patient is at a low activity level and disable such automatic adjustments when the patient is at a high patient activity level. Such activity determinations may rely solely or in part on a timer that infers activity due to time (e.g., time of day). Thus, such a method may disable while the patient is awake (daytime) and enable while the patient is asleep (nighttime). A care provider may determine exact times or conditions to enable or disable. Such a method can reduce discomfort associated with changes to one or more biventricular pacing therapy parameters.

An exemplary implantable device (see, e.g., the device 100 of FIGS. 1 and 2) may include a power source, a patient activity sensor (and/or timer), a processor powered by the power source, memory accessible by the processor and control logic, operable through use of the processor, to implement the aforementioned exemplary method. For example, such control logic may call for delivery of biventricular pacing therapy using an AV delay and a VV delay, determine a patient activity level using the patient activity sensor and enable or disable automatic adjustment of the AV delay or the VV delay based at least in part on one or more patient activity levels.

As already mentioned, many CRT patients respond negatively to changes in timings, especially where AV or PV delay is shortened (e.g., 80 ms or less). Conventional loss of capture algorithms call for shortening AV or PV to avoid fusion, which can have uncomfortable consequences. Thus, as described herein, fusion detection occurs to help ensure that loss of capture is not due to fusion and, where it is not due to fusion, fewer or no adjustments to timings may occur. Often a care provider spends significant time with a CRT patient to reach optimal settings. Thus, adjustments to these settings should occur on an as needed basis only.

What is claimed is:

1. A method comprising:
    delivering biventricular pacing therapy using an implantable medical device programmed with an AV delay and a VV delay wherein pacing occurs first in a master ventricle and second in a slave ventricle;
    detecting loss of capture in one of the ventricles;
    shortening the AV delay if the loss of capture occurred in the master ventricle; and
    shortening the VV delay if the loss of capture occurred in the slave ventricle.

2. The method of claim 1 wherein the shortening the AV delay reduces risk of fusion between a ventricular stimulus and an atrial event.

3. The method of claim 1 wherein the shortening the VV delay reduces risk of fusion between a ventricular stimulus and a ventricular event.

4. The method of claim 1 and further comprising calling for one or more capture threshold searches if loss of capture occurred in both ventricles.

5. An implantable device comprising:
    a power source;
    a circuit for acquisition of intracardiac electrograms;
    a processor powered by the power source;
    memory accessible by the processor; and
    control logic, operable through use of the processor, to call for delivery of biventricular pacing therapy using an AV delay and a VV delay wherein pacing occurs first in a master ventricle and second in a slave ventricle, to detect loss of capture in one of the ventricles based on at least one acquired intracardiac electrogram, to shorten the AV delay if loss of capture occurs in the master ventricle, and to shorten the VV delay if loss of capture occurs in the slave ventricle.

6. An implantable device comprising:
    means for delivering biventricular pacing therapy using an AV delay and a VV delay wherein pacing occurs first in a master ventricle and second in a slave ventricle;
    means for detecting loss of capture in one of the ventricles; and
    means for shortening the AV delay if the loss of capture occurred in the master ventricle; and
    means for shortening the VV delay if the loss of capture occurred in the slave ventricle.

7. The implantable device of claim 6 and further comprising means for calling for one or more capture threshold searches if loss of capture occurred in both ventricles.

8. A method comprising:
    delivering biventricular pacing therapy using an implantable medical device programmed with one or more timing parameters, wherein pacing occurs first in a master ventricle and second in a slave ventricle;
    detecting for loss of capture in one or both of the ventricles;
    if loss of capture is detected in one of the ventricles, detecting for fusion with respect to that ventricle; and
    if fusion is detected, calling for fusion avoidance, wherein fusion avoidance shortens an interventricular delay if loss of capture occurs in the slave ventricle and shortens an atrio-ventricular delay if loss of capture occurs in the master ventricle.

9. The method of claim 8 further comprising:
    after shortening the interventricular delay, detecting for loss of capture in the slave ventricle; and
    if capture is lost, shortening the atrio-ventricular delay.

10. The method of claim 9 further comprising:
    after shortening the atrio-ventricular delay, detecting for loss of capture in the slave ventricle; and
    if loss of capture in the slave ventricle is still detected, performing a threshold search for the slave ventricle.

11. The method of claim 8 further comprising:
    after shortening the atrio-ventricular delay, detecting for loss of capture in the master ventricle; and
    if loss of capture in the master ventricle is still detected, performing a threshold search for the master ventricle.

* * * * *